United States Patent [19]

Kopolow et al.

[11] Patent Number: 5,130,121
[45] Date of Patent: * Jul. 14, 1992

[54] SKIN CARE COMPOSITIONS CONTAINING DISCRETE MICRODROPLETS OF AN OIL IN WATER STABILIZED BY IN SITU POLYMERIZATION OF WATER-SOLUBLE VINYL MONOMER

[75] Inventors: Stephen L. Kopolow, Plainsboro; William J. Burlant, Wayne; Michael W. Helioff, Westfield; Carmen D. Bires, Hackettstown; Robert B. Login, Oakland, all of N.J.; Mohammed Tazi, Marietta, Ga.

[73] Assignee: ISP Investments Inc., Wilmington, Del.

[*] Notice: The portion of the term of this patent subsequent to Dec. 17, 2008 has been disclaimed.

[21] Appl. No.: 638,596

[22] Filed: Jan. 8, 1991

Related U.S. Application Data

[63] Continuation-in-part of Ser. No. 510,017, Apr. 17, 1990, abandoned, and a continuation-in-part of Ser. No. 604,263, Oct. 29, 1990, Pat. No. 5,073,296.

[51] Int. Cl.$^5$ ............................ A61K 7/15; B01J 13/00
[52] U.S. Cl. ............................ 424/47; 252/312; 252/89.1; 424/71; 424/73; 424/70; 424/59; 424/65; 514/557; 514/772.7; 514/847
[58] Field of Search ............... 252/312, 89.9; 424/73, 424/59, 71, 70; 514/557, 772.7, 847

[56] References Cited

U.S. PATENT DOCUMENTS

| | | | |
|---|---|---|---|
| 4,923,695 | 5/1990 | Nowak, Jr. et al. | 424/71 |
| 4,933,170 | 6/1990 | Nowak, Jr. et al. | 424/67 |
| 4,940,576 | 7/1990 | Walsh | 424/70 |
| 5,034,220 | 7/1991 | Helioff et al. | 424/73 |

Primary Examiner—Richard D. Lovering
Assistant Examiner—N. Bhat
Attorney, Agent, or Firm—Walter Katz; Marilyn J. Maue; Joshua J. Ward

[57] ABSTRACT

What is provided herein are skin care compositions containing discrete microdroplets of an oil in water stabilized by in situ polymerization of a water-soluble vinyl monomer. The discrete microdroplets are prepared by dispersing the oil, preferably a silicone, in water, adding the water-soluble vinyl monomer, preferably vinylpyrrolidone, and polymerizing the monomer in situ such that the oil is stabilized in the resulting polymer solution as discrete microdroplets.

28 Claims, No Drawings

SKIN CARE COMPOSITIONS CONTAINING DISCRETE MICRODROPLETS OF AN OIL IN WATER STABILIZED BY IN SITU POLYMERIZATION OF WATER-SOLUBLE VINYL MONOMER

CROSS-REFERENCE TO RELATED PATENT APPLICATIONS

This application is a continuation-in-part of copending U.S. applications Pat. Ser. No. 510,017, filed Apr. 17, 1990, now abandoned and Ser. No. 604,263, filed Oct. 29, 1990, now U.S. Pat. 5073296, respectively, and assigned to the same assignee as herein.

BACKGROUND OF THE INVENTION

1. Field of the invention

This invention relates to skin care compositions containing stable, discrete microdroplets of an oil in water stabilized by a water-soluble polymer solution, and more particularly to new and improved cosmetic compositions for the care of the skin.

2. Description of the Prior Art

The unique properties of many oils make it desirable to include them in aqueous-based cosmetic compositions. For example, cosmetically-active materials such as silicone oils, fluids and gums, mineral oils, and water-insoluble organic esters such as isopropropyl palmitate and isopropyl myristate, are particularly useful in cosmetic formulations for the hair and skin. In these compositions, the lubricity properties of the cosmetically-active materials impart conditioning action for the user. However, such oils are immiscible with water which makes it very difficult to maintain a stable aqueous dispersion without rapid separation of the composition into oil and water phases. To solve the problem of providing effective dispersibility of such materials in water, it has been necessary in the past to include a surfactant in aqueous cosmetic compositions containing cosmetically-active oils in order to maintain dispersed droplets of the oil in the aqueous solution. However, the use of surfactants increases the cost of the product and may effect the quality of the composition. In addition, even with a surfactant present, the stability of the dispersion is often not completely satisfactory. See, for example, U.S. Pat. Nos. 3,957,970; 4,472,375; 4,559,227; 4,586,518; 4,728,457; 4,741,855; 4,749,565; 4,749,732; 4,788,006; and 4,849,127.

However, these and other processes have not provided a composition in which cosmetically active oils, such as silicone oils, are present as a stable dispersion in an aqueous medium. Nor does the prior art suggest a procedure for allowing such oils to maintain themselves in stable condition in an aqueous cosmetic formulation.

Accordingly, it is an object of the present invention to provide a cosmetic composition having a stabilized oil in water therein, preferably in the form of microdroplets, which can be maintained discretely and for an extended period of time.

Another object of this invention is to provide a method for preparing an aqueous skin care composition which includes stable, discrete microdroplets of a silicone oil dispersed therein.

Still another object of the present invention is to provide a method of preparing a skin care composition in which microdroplets of silicone oil are homogeneously distributed in the composition.

Yet another object is to provide a skin care composition in which stable, dispersed microdroplets are prepared by in situ polymerization of a water-soluble vinyl monomer, such as vinylpyrrolidone, in the presence of dispersed droplets of a water-insoluble oil, such as silicone oil, in water.

Among the other objects of the invention is to provide a skin care formulation containing stable, discrete microdroplets of a cosmetically-active oil stabilized in an aqueous solution of in situ polymerized vinylpyrrolidone.

These and other objects and features of the invention will be made apparent from the following description thereof.

Abbreviations and Definitions

Oil—A compound which is a water-insoluble liquid at room temperature and has an oily consistency Cosmetically-active oil—An oil which imparts a particularly desirable property, e.g. lubricity, to a cosmetic formulation VP—Vinylpyrrolidone PVP—Polyvinylpyrrolidone DM—Polydimethylsiloxane, Dimethicone, 100 cs, Petrarch Chem. Co; 1000 cs, Dow Corning Corp.

MO—Mineral oil

TBP—Tert-butyl peroctoate, e.g. Trigonox®21 (AKZO Chem. Co.)

TBPP—t-Butylperoxy pivalate, e.g. Lupersol 11 (Atochem N.A.)

Brookfield viscosity—Viscosity of Stabilized Oil in Water Product in cps, as measured using a RVT spindle # 3 @70 rpm

SUMMARY OF THE INVENTION

What is provided herein is a cosmetic composition for the care of the skin containing stable, discrete microdroplets of a cosmetically-active oil in water stabilized in a polymer solution of an in situ polymerized, water-soluble vinyl monomer. The stable, discrete, microdroplets are prepared by dispersing the oil in water to form microdroplets, adding a water-soluble vinyl monomer, such as vinylpyrrolidone and polymerizing the monomer in situ such that the oil droplets are stabilized in the resultant aqueous polymer solution.

In the preferred form of the invention, the cosmetically-active oil is a silicone oil, a mineral oil or a water-insoluble ester such as isopropyl myristate and isopropyl palmitate.

Suitably the dispersion is present in an amount of about 0.1 to 25 weight percent of the composition, preferably about 1 to 10 weight percent, of the skin care composition.

DETAILED DESCRIPTION OF THE INVENTION

The active material to be dispersed is a cosmetically-active oil which is a water-insoluble liquid at room temperature, and which imparts a particularly desirable property to skin care cosmetic formulations. Such cosmetically-active oils include silicone oils, mineral oils and water-insoluble esters such as isopropyl myristate and isopropyl palmitate.

Suitable silicone oils or fluids for use in the invention may be selected from non-volatile polyalkyl siloxanes, polyaryl siloxanes, polyalkylaryl siloxanes and polyether siloxane copolymers. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued July 20, 1970. Preferably, the viscosity of these siloxanes selected have a viscosity of about 100 to about 100,000 cs, and most preferably, a viscosity of up to about 15,000 cs.

Suitable non-volatile polyalkylaryl siloxanes include, for example, polymethylphenyl siloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Other suitable oils for use herein include cosmetically-active materials such as light and heavy mineral oils, and water-insoluble organic esters such as isopropyl palmitate and isopropyl myristate.

In the practice of the present invention, the oil to be dispersed is first added to water and then subjected to agitation to produce a fine dispersion of discrete oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer such as vinylpyrrolidone itself or a derivative thereof such as an alkyl vinyl pyrrolidone, is added to the mixture, along with an appropriate free radical polymerization initiator.

Suitable free radical polymerization initiators for polymerization of water-soluble vinyl monomers include such free radical catalysts as t-butylperoctoate, t-butylperoxy- pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the oil.

As the polymerization proceeds, the dispersed oil droplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

The production of stable, discrete microdroplets of oil in the resulting aqueous polymer solution can be controlled by the viscosity of the aqueous polymer solution. For example, the viscosity of this medium can be increased by increasing the relative amount of vinyl monomer to oil in the original reaction mixture. By increasing the viscosity of the polymer solution, the tendency to form a stable, homogeneous suspension of discrete microdroplets of oil throughout the entire medium is enhanced. On the other hand, reducing the viscosity of the medium by decreasing the amount of vinyl monomer in the initial mixture results in a more dilute concentration of polyvinyl polymer in the resultant mixture, which enhances the tendency to form a separate layer of discrete oil droplets.

Suitably, the ratio of monomer to oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized oil in water product, for example, polyvinylpyrrolidone polymer which is, obtained by in situ polymerization of vinylpyrrolidone monomer, suitably is in the range of about 3,000 to 100,000 cps, preferably about 4,000 to 60,000 cps, and most preferably, about 6,000 to 25,000 cps.

The diameter of the oil microdroplets obtained are observed to be in the range of about 0.1 to 450 microns, and usually are about 1 to 100 microns.

The skin care cosmetic compositions in accordance with the present invention containing the discrete, cosmetically-active oil dispersion as defined above can be provided under different forms.

The skin care cosmetic compositions according to the invention can contain the dispersion either as the principal active component or as an additive.

Moreover, these compositions generally contain at least one conventional adjuvant used in cosmetic compositions.

The skin care cosmetic compositions can be provided in the form of aqueous, alcoholic or hydroalcoholic solutions, the alcohol being principally a lower alkanol such as ethanol or isopropanol, or in the form of a cream, a gel, an emulsion or even in the form of an aerosol packaged under pressure in an aerosol container together with a propellant.

The adjuvants generally provided in the cosmetic compositions according to the invention are, for example, perfumes, dyes, preservatives, sequesterants, thickening agents and the like.

The cosmetic compositions according to the invention are either compositions ready for use or concentrates which can be diluted before use.

The cosmetic compositions according to the invention are not limited to a particular concentration of the dispersion described above.

Generally, in the cosmetic compositions according to the invention, the concentration of the PVP-silicone oil dispersion is between 0.1 and 25 weight percent and preferably between 1 and 10 weight percent.

As has been indicated above, the dispersion of the cosmetically-active oil in the cosmetic composition of the invention imparts principally advantageous cosmetic characteristics when they are applied to the skin of the user.

The skin care cosmetic compositions in accordance with the invention are characterized by the fact that they contain stable, discrete microdroplets of a cosmetically-active oil in the form of a dispersion.

These cosmetic compositions for the skin can be provided in the form of aqueous, alcoholic or hydroalcoholic solutions, the alcohol being either ethanol or isopropanol, preferably in the form of a cream, a mousse, a lotion, an oil, a water-in-oil emulsion or even in the form of a spray. In this latter case, the compositions are packaged in an aerosol container, under pressure, together with a propellant such as nitrogen, nitrous oxide, carbon dioxide butane or even mixtures of such propellants.

As has been indicated above, the cosmetic composition according to this invention is preferably employed for the care or treatment of the skin.

In effect, these compositions facilitate the hydration of the skin and avoid its drying out. These compositions also impart to the skin excellent softness to the touch.

The cosmetic compositions for the skin are provided preferably in the form of lotions, creams, gels, emulsions, mousses or aqueous, alcoholic or hydroalcoholic solutions.

The adjuvants generally present in these cosmetic compositions are, for example, perfumes, dyes, preservatives, thickening agents, sequesterants, emulsifiers, solar filters and the like.

These compositions for the skin constitute principally treating creams or lotions for the hands, face or body, sunscreens, cleansing lotions or foamable bath liquids and deodorant and antiperspirant compositions.

These compositions are prepared according to known methods.

For example, to obtain a cream, an aqueous phase containing in solution the dispersion and optionally other components or adjuvants is emulsified with an oily phase.

The oily phase can be constituted by various compounds such as, for example, paraffin oil, petrolatum oil, sweet almond oil, avocado oil, olive oil, esters of fatty acids such as glyceryl monostearate, ethyl or isopropyl palmitates, alkyl myristates such as propyl, butyl or cetyl myristates. Fatty alcohols such as cetyl alcohol or waxes such as beeswax can also be added.

The dispersion can be present in these cosmetic compositions for the skin as an additive or as the principal active component.

The following non-limiting examples are provided to illustrate the invention Unless otherwise stated, all parts and percentages are by weight.

The invention will now be described with references to the following more particular examples.

EXAMPLE 1

The in situ polymerization process of the invention was carried out in a 1-liter laboratory reactor equipped with an overhead stirring motor, a metal anchor agitator, a nitrogen gas inlet tube, a water condenser connected to a bubbler, a temperature probe connected to a temperature controller and associated with a heating mantle, and a dropping funnel.

The reactor first was purged with nitrogen and charged with 400 g. of distilled water and 10 g. of Dimethicone oil having a viscosity of 100 cs. The oil-water then mixture was agitated vigorously at 350 rpm under nitrogen for 30 minutes whereupon the oil was dispersed as transparent, discrete microdroplets in the aqueous medium. The dispersion then was heated to 80° C. and 0.25 g. of di-tert-butylperoctoate was added. At this point, the mixture was maintained for 30 minutes with continuous stirring whereafter 90 g. of vinylpyrrolidone and an additional 0.25 g. of di-tert-butylperoctoate was added at one time while maintaining a nitrogen flow of 15 ml/min. After about 10–15 minutes, an exotherm was observed and the temperature increased to 86° C. The transparent, spherical droplets of oil became opaque. The the temperature was reduced to 80° C. and polymerization was continued for 6–8 hours with stirring. During this period, the dispersion became milky and the droplets became completely invisible. Polymerization was considered complete when the measured residual monomer content was less than 0.1%.

The composition obtained was a stable, homogeneous dispersion of microdroplets of Dimethicone oil stabilized in an aqueous polyvinylpyrrolidone solution. Upon exerting only slight pressure on the microdroplets, the silicone oil was observed to ooze out. However, the composition was quite stable for many months at room temperature, and for an extended period at the elevated temperature of 45° to 54° C.

EXAMPLES 2-3

The procedure of Example 1 was repeated using weight ratios of 80 g. of vinylpyrrolidone to 20 g. of Dimethicone oil (Example 2), and 70 g. of vinylpyrrolidone to 30 g. of Dimethicone oil (Example 3). Similar results to Example 1 were obtained in these runs.

EXAMPLE 4

The procedure of Example 1 was followed using a weight ratio of 20 g. of vinylpyrrolidone and 80 g. of Dimethicone oil. The resultant composition was not as viscous as in Example 1. The microdroplets obtained remained in discrete form, however, without coalescence, but settled to the bottom of the solution as a separate layer.

EXAMPLE 5

The procedure of Example 1 was followed using a weight ratio of 135 g. of vinylpyrrolidone to 15 g. of Dimethicone oil in 600 ml. of water. The results were substantially the same as obtained in Example 1.

EXAMPLE 6

The procedure of Example 1 was followed using a weight ratio of 135 g. of vinylpyrrolidone to 15 g. of a Dimethicone oil having a viscosity of 1,000 cs (mol. wt. of 28,000). The mixture was agitated at 700 rpm to produce a stable dispersion of the viscous silicone oil droplets in the aqueous polymer solution.

EXAMPLE 7

A pilot plant run was carried out in a 30 gal. reactor using two wide span turbine agitators having pitched and flat blades set at 200 rpm. 10,790 g. of vinylpyrrolidone, 1205 g. of Dimethicone oil, 100 cs, 48,225 g. of water, 120 g. of di-t-butylperoctoate, and 317 g. of Germaben ® preservative were used in this run. After 6 hours, polymerization was complete and a stable, homogeneous, milky aqueous dispersion of discrete, coated silicone oil droplets was obtained which dispersion remained in discrete and suspended form throughout the composition. The composition also was stable for an extended period of time.

EXAMPLE 8

The procedure of Example 1 was followed using 90 g. of vinylpyrrolidone, 10 g. of Dimethicone oil, 100 cs, 400 g. of water and 0.75 g. of Lupersol 11. The results were similar to those obtained in Example 4.

EXAMPLE 9

The procedure of Example 1 was followed 90 g. of vinylpyrrolidone, 10 g. of light mineral oil having a density of 0.838 g/ml, 400 g. of water and 0.75 g. of Lupersol 11. The results were similar to Example 1.

EXAMPLE 10

The procedure of Example 9 was followed using 10 g. of heavy mineral oil having a density of 0.862 g/ml. The results were similar to Example 9.

TABLE I

| Ex. No. | Monomer | Amt (g) | Silicone Oil | Amt (g) | Viscosity (cs) | MW |
|---|---|---|---|---|---|---|
| 1 | VP | 90 | DM | 10 | 100 | 5970 |
| 2 | VP | 80 | DM | 20 | 100 | 5970 |
| 3 | VP | 70 | DM | 30 | 100 | 5970 |
| 4 | VP | 20 | DM | 80 | 100 | 5970 |
| 5 | VP | 135 | DM | 15 | 100 | 5970 |
| 6 | VP | 135 | DM | 15 | 1000 | 28,000 |
| 7* | VP | 10,790 | DM | 1205 | 100 | 5970 |
| 8 | VP | 90 | DM | 10 | 100 | 5970 |

TABLE I-continued

| Ex. No. | Monomer | Amt (g) | Silicone Oil | Amt (g) | Viscosity (cs) | MW |
|---|---|---|---|---|---|---|
| 9 | VP | 90 | MO | 10 | | |
| 10 | VP | 90 | MO | 10 | | |

TABLE I-A

| Ex. No. | Comonomer | Amt (g) | Medium | Amt (g) | Initiator | Amt (g) | Agitation (rpm) |
|---|---|---|---|---|---|---|---|
| 1 | — | — | Water | 400 | TBP | 0.75 | 350 |
| 2 | — | — | Water | 400 | TBP | 0.75 | 350 |
| 3 | — | — | Water | 400 | TBP | 0.75 | 350 |
| 4 | — | — | Water | 400 | TBP | 0.75 | 350 |
| 5 | — | — | Water | 600 | TBP | 0.76 | 350 |
| 6 | — | — | Water | 600 | TBP | 0.76 | 700 |
| 7* | — | — | Water | 48,225 | TBP | 120 | 200 |
| 8 | — | — | Water | 400 | TBPP | 0.75 | 350 |
| 9 | — | — | Water | 400 | TBP | 0.75 | 350 |
| 10 | — | — | Water | 400 | TBP | 0.75 | 350 |

*Pilot plant run

TABLE II

| Ex. No. | % Solids | Brookfield Viscosity (cps) | Diameter of Microspheres (microns) Mean | Range | Form of Composition |
|---|---|---|---|---|---|
| 1 | 19.7 | 7,200 | — | — | stable, homogeneous, milky dispersion of discrete microspherical droplets of silicone oil coated by polyvinylpyrrolidone polymer |
| 2 | 22.0 | 24,400 | | 1–14 | |
| 3 | 21.1 | 17,300 | | 1–17 | |
| 4 | 20.0 | — | | — | |
| 5 | | | | | |
| 6 | 20.6 | 10,200 | 56 | | |
| 7 | 20.2 | 8,900 | 80 | 3–54 | |
| 8 | 20.2 | 7,200 | — | — | |
| 9 | 20.45 | 4,770 | — | 0.4–13 | as in Ex. 1 |
| 10 | 21.00 | 3,180 | — | 0.5–29 | as in Ex. 1 |

The following examples are representative of cosmetic compositions of the present invention.

LOTION FOR DRY SKIN

| Essential | (% by Wt.) Suitable | Preferred | Optimum |
|---|---|---|---|
| PVP-Silicone (90/10, Ex. 1) (20% solids) | 0.5–10 | 1–5 | 3.0 |
| Stabilizer | 0.05–0.5 | 0.1–0.3 | 0.15 |
| Emulsifier | 1–10 | 2–8 | 3.0 |
| Soap | 1–10 | 2–8 | 3.0 |
| Wax | 0–10 | 3–8 | 5.0 |
| Neutralizer | 0.2–1 | 0.4–1 | 1.0 |
| Water | qs | qs | qs |

The following is a specific example of the lotion for dry skin composition of the invention.

| Ingredient | % by weight |
|---|---|
| Distilled water | 85.10 |
| Polyacrylic acid (crosslinked) | 0.15 |
| Stearic acid, XXX | 3.00 |
| Mineral oil, 70 cts | 2.00 |
| Emulsifying wax | 3.00 |
| PVP-Silicone (90, 10 Ex. 1) (20% solids) | 3.00 |
| Oleth-20 | 1.50 |
| Triethanolamine | 1.00 |
| Methylparaben/propylparaben | 1.00 |
| Fragrance | 0.25 |

| Ingredient | % by weight |
|---|---|
| | 100.00 |

The presence of the PVP-silicone in the lotion enhances the smoothness, softness and silky feel of the skin.

The following are other representative skin care compositions in which the presence of PVP-silicone is advantageous for the user.

BATH PREPARATION

| | |
|---|---|
| PVP-Silicone (Ex. 1) | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocyl taurate | 20.0 |
| aloe vera gel | 1.0 |
| coconut oil | 1.0 |
| glycol stearate | 1.0 |
| deionized water | qs |
| preservative | qs |
| colorant | qs |

SUSCREEN LOTION (1)

| | |
|---|---|
| PVP-Silicone (Ex. 1) | 2.5 |
| sorbitol | 6.0 |
| propylparaben | 1.0 |
| glyceryl stearate | 2.4 |
| stearic acid | 1.5 |
| octyl dimethyl PABA | 7.5 |
| benzophenone-3 | 2.5 |
| lanolin | 2.5 |
| methylparaben | 0.2 |
| deionized water | qs |

SKIN CLEANSER FOR OILY SKIN

| | |
|---|---|
| PVP-Silicone (Ex. 1) | 2.5 |
| propylene glycol | 5.0 |
| hydroxyethylcellulose | 0.9 |
| sodium laureth sulfate (30% active) | 15.0 |
| preservative | 0.75 |
| germacidal agent | 6.0 |
| water | qs |

MOISTURIZING LOTION

| | |
|---|---|
| PVP-Silicone (Ex. 1) | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

CATIONIC MOUSSE HAND/BODY LOTION
(Used 85 Parts of the following formula to 15 parts propellant A-46)

| | |
|---|---|
| PVP-Silicone (Ex. 1) | 0.50 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |

AFTER SHAVE BALM

| | |
|---|---|
| PVP-Silicone (Ex. 1) | 1.00 |
| Carbomer 941 | 0.20 |
| tetrasodium ethylene diamine tetracetic acid | 0.10 |
| cetearyl alcohol* polyethylene glycol ether of cetearyl alcohol | 2.50 |
| isopropyl myristate | 1.00 |
| Oleth-20 | 1.00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |

*50/50 mixture of cetyl and stearyl alcohols

SELF-HEATING AEROSOL SHAVING CREAM
(Used dual dispensing valve containing 30 ml of 3% hydrogen peroxide)

| | |
|---|---|
| PVP-Silicone (Ex. 1) | 2.00 |
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |

ANTIPERSPIRANT STICK

| | |
|---|---|
| PVP-Silicone (Ex. 1) | 10 |
| stearyl alcohol | 20 |
| cyclomethicone | 40 |
| aluminum chlorhydrate | 20 |
| acetylated sucrose distearate | 2.5 |
| talc | 1.5 |
| amorphous fused silica | 2 |
| myristyl ether PM-3 | 3 |
| polyoxyethylene glycol stearate | 1 |

What is claimed is:

1. A skin care composition containing a stabilized cosmetically-active product obtained by in situ polymerization of a water-soluble vinyl monomer in the presence of discrete microdroplets of a cosmetically-active oil in water.

2. A skin care composition according to claim 1 wherein said water-soluble vinyl monomer is vinyl pyrrolidone.

3. A skin care composition according to claim 2 wherein the weight ratio of the vinylpyrrolidone monomer to silicone in the polymerization mixture is about 95:5 to 5:95, respectively, on a weight basis.

4. A skin care composition according to claim 3 wherein said weight ratio is about 90:10 to about 50:50.

5. A skin care composition according to claim 2 wherein the Brookfield viscosity of the stabilized oil in water product obtained upon in situ polymerization is about 3,000 to 100,000 cps.

6. A skin care composition according to claim 1 wherein said stabilized microdroplets are homogeneously distributed throughout the resulting polymer solution.

7. A skin care composition according to claim 1 wherein said cosmetically-active oil is a silicone having a viscosity between about 5 to 600,000 cs.

8. A skin care composition according to claim 7 wherein said silicone has a viscosity between about 100 and 100,000 cs.

9. A skin care composition according to claim 7 wherein the particle sizes of the stabilized, discrete microdroplets of silicone are in the range of about 0.1 to 450 microns in diameter.

10. A skin are composition according to claim 9 wherein said diameter of said particles is about 1 to 100 microns, and said Brookfield viscosity of the stabilized silicone in water product is about 4,000 to 60,000 cops.

11. A skin care composition according to claim 10 wherein said Brookfield viscosity is about 6,000 to 25,000 cps.

12. A skin care composition according of claim 7 wherein said silicone is a on-volatile polyalkyl siloxane, a polyaryl siloxane, a polyalkylaryl siloxane or a polyether siloxane.

13. A skin care composition according to claim 12 wherein said silicone oil is a polydimethyl siloxane.

14. A skin care composition according to claim 1 wherein said sin situ polymerization is carried out at a temperature of about 55° to about 85° C.

15. A skin care composition according to claim 1 wherein the free radical polymerization initiator is oil soluble.

16. A skin care composition according to claim 1 wherein in situ polymerization is carried out under vigorous agitation of the polymerization mixture until a milky suspension is obtained and the residual monomer content of the product is less than about 0.5%.

17. A skin care composition according to claim 1 which is a lotion for dry skin.

18. A skin care composition according to claim 1 which is an antiperspirant stick.

19. A skin care composition according to claim 1 which is a cleansing composition.

20. A skin care composition according to claim 1 which is a bath preparation.

21. A skin care composition according to claim 1 which is a self-heating aerosol shaving cream.

22. A skin care composition according to claim 1 which is an after shave balm.

23. A skin care composition according to claim 1 which is a cationic mousse hand/body lotion.

24. A skin care composition according to claim 1 which is a moisturizing lotion.

25. A skin care composition according to claim which is a sunscreen lotion.

26. A skin care composition according to claim 1 which is a bubble bath.

27. A skin care composition according to claim 1 wherein said product is present in an amount of about 0.1 to 25 weight percent of the composition.

28. A skin care composition according to claim 27 wherein said amount is about 1 to 10 weight percent of the composition.

* * * * *